Oct. 11, 1955 J. D. BROWNELL Plant Pat. 1,425
ROSE PLANT
Filed March 17, 1953
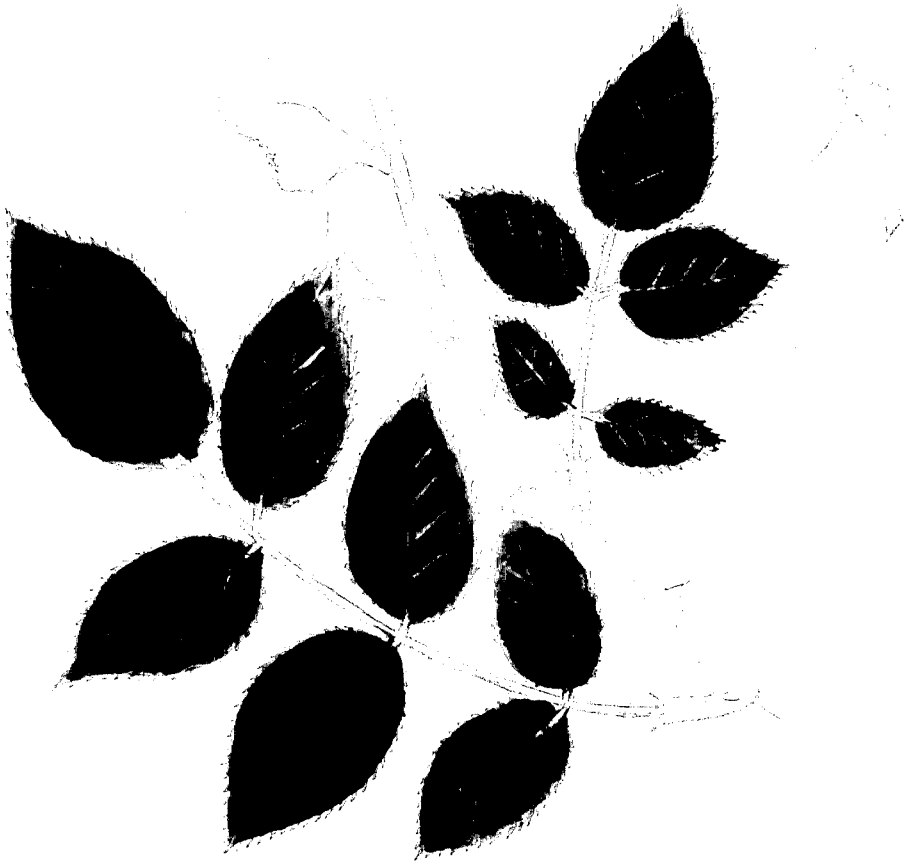
INVENTOR,
Josephine D. Brownell.

United States Patent Office

Plant Pat. 1,425
Patented Oct. 11, 1955

1,425

ROSE PLANT

Josephine D. Brownell, Little Compton, R. I.

Application March 17, 1953, Serial No. 343,008

1 Claim. (Cl. 47—61)

My invention relates to rose plants, and especially to a new, original and distinct variety of the class known commercially as "hybrid teas" and is a variant in that class, being a *Rosa wichuraiana* hybrid tea hybrid, in combination with cane growth usually common to climbing roses only, except the canes of my new rose plant usually bear terminal flowers and recurrent blooms on branches therefrom, often the same year that the canes grow; produced by me and under my direction in the breeding grounds of my research gardens in Little Compton, Rhode Island, by selection of variety variations and by cross pollenation; which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States:

The medium to deep pink shades (ordinary dictionary definition) of its petals, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers, notable after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming;

And especially its characteristic of partial freedom from premature defoliation by black-spot, under certain definite conditions of exposure, without any cultural control.

In the accompanying drawing forming a part of this specification I have shown my new rose in its natural colors, that is, as near as is possible to do so artificially.

The picture represents a bloom near the terminal end of a cane growth as it blooms the same season as the growth of the cane.

My new rose is otherwise described as follows:

ESSENTIAL INFORMATION

*Type*

Hybrid tea, *Rosa wichuraiana* hybrid; hybrid tea to ascending to tall to climber, for garden display, cut flower and forcing or growing under glass.

*Class*

Hybrid tea crossed with *Rosa wichuraiana,* further restricted by originator to include only those varieties that can survive moderately low sub-zero temperatures.

*Breeding*

This variety was produced and bred by me and under my direction by propagation, selection and cross pollenation.

It came into being as a seedling grown from a seed borne on a plant of an unnamed seedling not patented and the pollen parent was Queen o' the Lakes, Plant Patent No. 1003.

The pollenation that fertilized the seed that grew into my new rose, as well as the two previous pollenations that produced its two parents, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 9, 1949.[1] The seed was planted for me and under my direction on December 20, 1949, and the date of the first flower was July 1, 1950.

I have since made and directed extensive propagations and tests of this plant and flower.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August 1950 and the characters have successively reproduced, true to original seedling.

FLOWER

*Habit*

It blooms out of doors in Little Compton, beginning about three days prior to the average beginning time of commercial hybrid teas and continuous relative to growth of the plant until frost.

*Flowers borne*

Often one and frequently two or three and occasionally more on each stem, in the usual hybrid tea type of cluster, and frequently on climber canes as they grow. Such canes terminate in one or more blooms or clusters of blooms.

All of the foregoing bloom expression usually obtains the first year after budding on maidens and on two year old plants the first growing season after being transplanted.

The routine performance thereof is usually as follows. The plant first blooms like a hybrid tea, followed by cane growths in length from about four to five feet, later more in length terminating in blooms. The hybrid tea growth continues to grow rebloom stems in the hybrid team manner until frost, also similar stems from the cane growths.

Occasionally cane growth will grow from the hybrid tea growth, canes branch from the canes.

The canes seek to grow at an angle of about 90° from the horizontal.

The hybrid tea growth can usually be differentiated from cane growth by the diameters thereof and otherwise by characteristics common to each.

The pedicels and peduncles are medium in diameter and medium in length, erect, stiff, almost smooth, free from large prickles and bristles. Stems are long, diameter medium and notably stiff and rigid.

*Quantity of bloom*

Free, being cumulative in quantity from year to year

[1] This and other dates herein are approximate.

as the plant increases in size, flowering through the summer and fall.

*Fragrance*

Distinctive, pleasing China tea in combination with that of *Rosa wichuraiana,* under favorable environment.

*Bud*

Neck normal as described, opens well, being little to not at all affected by hot or wet weather or both, as to color and form, except at very high temperatures the color is less intense and the form of the petals is less recurled.

Before the calyx breaks the size is medium, form moderately high pointed, the sepals are usually normal and regular, tapering to lanceolate at their apex, without foliaceous appendages, turning back nearly perpendicular to the pedicel as the bud opens, usually no spurs on sides.

Color of the bud as the calyx opens, outer side of petals nearly Geranium Lake at 20/1, overlaid slightly with Lemon Yellow and near the base Lemon Yellow at 4/1; inner side of petals same except less pronounced; color reference to English Horticultural Color Chart.[2]

*Bloom*

Color same, Geranium Lake gradually softening to Geranium Lake at 20/1.

Color slightly variable dependent upon quality of sun or other light.

The flower usually varies in size between three and one-half inches and four and one-half inches in diameter when fully open, petals average in number from 35 to 50, frequently some smaller petals and petaloids in the center, variable in number.

The flower opens moderately ovoid and semi-high centered, nearly formal, with display of stamens and pistils when fully open. The petals are variable from obovate to ovate. Texture is medium to thick; both sides brilliant. The time of opening in favorable conditions is about five days.

The petals are substantial and after about seven days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Reproductive organs*

Stamens, quantity variable, medium long or slightly uneven length.

Anthers, nearly Marigold Orange at 11/3. Filaments, nearly Tangerine Orange at 9/3. Number variable around 30.

Pistils are several of nearly even length, averaging about one-half inch long, few in number.

Sepals are persistent and break off easily.

PLANT

*Foliage*

Is abundant, of compound leaves of three to five leaflets near the flower, five leaflets lower down the stem and frequently seven leaflets in the middle of the stems and canes and nearer the base. Often with short narrow leafy formations variously positioned near the flower as shown. Size of leaflets medium, averaging in size larger than most varieties of this type and as or nearly as large

[2] Color reference to same unless otherwise indicated.

as leaflets on most hybrid teas. Form of leaflets usually ovate with apex moderately acute, base rounded to slightly pointed in some instances with the circumference on one side of the petiolule out of alignment with the other side by about one-sixteenth of an inch or less, margins with slightly irregular small pointed serrations, petiolules short.

The leaflets average in width about one-half to two-thirds of their length.

Color of leaflets on the upper surface is slightly variable from Scheeles Green at 860, irregularly shaded with Spinach Green at o960/1, with reverse side nearly Asphodel Green frequently overlaid with trace of Dahlia Carmine, the last two color references are to Robert Ridgway Color Standards.

The rachises are medium, moderately narrow to slender, upper side smooth except some very short hairs on edge. Under side moderately smooth, usually three to five short prickles.

Stipules are long, averaging about one inch long or a little less, with sharp point, the upper edges of which normally form an angle of about 90 degrees.

Habit, hybrid tea, becoming bushy to tall; upright, compact, climbing by canes and more cumulative in growth from year to year than the normal hybrid tea rose plant, and with canes that branch to normal height of average hardy climber, by stems from the base and by rebranching and growth and enlargement and extension of the stems from the base. The growth is moderately free at first, developing more rapidly after one or two years under favorable vegetative opportunity.

Color of mature stems is Scheeles Green at 860/3, shading variously lighter and also occasionally with slight overlay of Spinel Red at oo23/1 variable in intensity, usually more pronounced on the sunny side.

Prickles, several, frequently two to four between leaves, averaging in length about one-quarter to one-third inch, shading from Crimson at 22 to lighter at the base, turning lighter throughout and later to nearly colorless.

*Winter resistance*

A notable characteristic of this new rose is the resistance to moderate sub-zero temperatures in combination with its hybrid tea character, its climbing habit and its *Rosa wichuraiana* ancestry. The word "temperature" herein refers to the Fahrenheit scale.

*Comparisons*

The variety most nearly resembling my new rose is Climbing Break o' Day, Plant Patent No. 696, which lacks some of the hybrid tea type of rebloom expressed by my new rose.

The color of my new rose is principally pink with yellow at the base of petals, as compared with Climbing Break o' Day which is Orange to Apricot, ordinary dictionary definition.

I claim:

The new and distinct variety of rose plant as described and illustrated, characterized by its color pattern, fragrance, form, and pink color of its bloom at the terminal end of canes that bloom the same season in which the canes grow; also, by the wichuraiana, hybrid tea, and everblooming climber characteristics, substantially as described.

No references cited.